US011974906B2

(12) United States Patent
Alzate Machado et al.

(10) Patent No.: US 11,974,906 B2
(45) Date of Patent: May 7, 2024

(54) ABSORBENT ARTICLE WITH MULTIPLE LAYERS

(71) Applicant: PRODUCTOS FAMILIA S.A., Medellin (CO)

(72) Inventors: Andrea Alzate Machado, Medellin (CO); Fabio Alberto López Pimienta, Medellin (CO); Juan Manuel Chamat, Medellin (CO)

(73) Assignee: Productos Familia S.A., Medellin (CO)

( * ) Notice: Subject to any disclaimer, the term of this patent is extended or adjusted under 35 U.S.C. 154(b) by 1231 days.

(21) Appl. No.: 16/662,572

(22) Filed: Oct. 24, 2019

(65) Prior Publication Data

US 2020/0054504 A1 Feb. 20, 2020

Related U.S. Application Data

(63) Continuation-in-part of application No. 14/660,169, filed on Mar. 17, 2015, now abandoned.

(30) Foreign Application Priority Data

May 27, 2014 (CO) .................................. 14-114349

(51) Int. Cl.
*A61F 13/47* (2006.01)
*A61F 13/20* (2006.01)
(Continued)

(52) U.S. Cl.
CPC ...... *A61F 13/5605* (2013.01); *A61F 13/2051* (2013.01); *A61F 13/4756* (2013.01); *A61F 13/4704* (2013.01)

(58) Field of Classification Search
CPC .... A61F 13/47; A61F 13/4707; A61F 13/472; A61F 13/47236; A61F 13/47245;
(Continued)

(56) References Cited

U.S. PATENT DOCUMENTS 5,599,339 A 2/1997 Horney
5,720,738 A 2/1998 Clark
(Continued)

FOREIGN PATENT DOCUMENTS

UY 4266 U 2/2010
WO 1996010978 A1 4/1996
(Continued)

OTHER PUBLICATIONS

Ministerio De Industria Energía Y Minería, Office Action, dated Oct. 19, 2022.
(Continued)

*Primary Examiner* — Catharine L Anderson
*Assistant Examiner* — Lynne Anderson
(74) *Attorney, Agent, or Firm* — The Morales Law Firm; Joseph L. Morales

(57) ABSTRACT

The present invention corresponds to an absorbent article comprising substrates having a top layer and a bottom layer, wherein the substrates are located one on top pf the other. The bottom substrate having attachment media located on the bottom layer, and the top substrate having support media located on the top end and bottom end of the top substrate. The bottom and op substrates are attached throughout the periphery thereof, and the top layer is permeable.

20 Claims, 12 Drawing Sheets

(51) Int. Cl.
*A61F 13/475* (2006.01)
*A61F 13/56* (2006.01)

(58) Field of Classification Search
CPC .............. A61F 13/47254; A61F 13/474; A61F 13/4756; A61F 13/505; A61F 13/5605; A61F 13/5611; A61F 13/5616
See application file for complete search history.

(56) References Cited

U.S. PATENT DOCUMENTS

| | | | | |
|---|---|---|---|---|
| 5,910,137 | A * | 6/1999 | Clark | A61F 13/474 |
| | | | | 604/389 |
| 6,013,064 | A | 1/2000 | Yamada | |
| 6,730,067 | B1 * | 5/2004 | Nukina | A61F 13/474 |
| | | | | 604/385.01 |
| 6,964,655 | B2 * | 11/2005 | Killeen | A61F 13/476 |
| | | | | 604/385.27 |
| 7,942,858 | B2 * | 5/2011 | Francoeur | A61F 13/4756 |
| | | | | 604/385.101 |
| 9,913,766 | B2 * | 3/2018 | Petersen | A61F 13/5605 |
| 9,980,856 | B2 * | 5/2018 | Wilson | A61F 13/474 |
| 2001/0027304 | A1 | 10/2001 | Mayer | |
| 2002/0138055 | A1 | 9/2002 | Motta et al. | |

FOREIGN PATENT DOCUMENTS

| | | |
|---|---|---|
| WO | 1997017797 A1 | 5/1997 |
| WO | 1998017220 A1 | 4/1998 |
| WO | 1999032062 A1 | 7/1999 |

OTHER PUBLICATIONS

Dirección Nacional De Propiedad Intelectual, Office Action, dated May 20, 2022.

* cited by examiner

ABSORBENT ARTICLE WITH MULTIPLE LAYERS

CROSS-REFERENCE TO RELATED APPLICATION

This is a continuation-in-part, and claims priority under 35 U.S.C. § 120, of U.S. patent application Ser. No. 14/660,169 filed Mar. 17, 2015, and entitled "ABSORBENT ARTICLE WITH MULTIPLE LAYERS"; which, in turn, claims priority under 35 U.S.C. § 119(a), from Colombian Application Serial Number 14-114349, filed on May 27, 2014, which are both incorporated herein by reference in their entirety.

FIELD OF THE INVENTION

The invention refers to an absorbent article comprising several substrates, with or without wings, located one on top of the other comprising one top permeable layer and one bottom impermeable layer bound together throughout the periphery. The absorbent article also comprises an absorbent core having different geometrical shapes.

BACKGROUND

Amongst the wide range of personal hygiene products available in the marketplace, there are the commonly used body fluid capture or retention products. Said absorbent articles, such as sanitary towels, daily protectors and incontinency absorbers are widely known and differ essentially in their shape, size, manufacturing process and absorption capacity.

Absorbent articles for female personal hygiene must be changed several times during the day, implying the user must discard the one in use and replace it with a new one. This in some occasions may generate inconvenience for the user, given a sufficiently private place is not always readily available for changing and in addition, several of these articles must be carried.

Several ways to solve this inconvenience have been disclosed. CO 08088369 describes a protector-type absorbent article having several removable layers with interdetachment media, in a way that every time the protector needs changing for a new one, the top layer is detached. However, said interdetachment medium causes the absorbent article to only have one position during use and thus, one sole possible place to detach the top layer. The proposed solution in the cited document is only described for daily protectors and does not address other absorbent articles such as sanitary towels.

In addition, female hygiene products disclosed in the art in most cases have been designed to fit a specific size of underwear reinforcement and not to the different shapes thereof, and thus when acquiring a product for normal underwear, it is not possible to be used for thong-type underwear or vice versa.

SUMMARY

The present invention refers to an absorbent article comprising substrates located one on top of the other comprising a top permeable layer and a bottom impermeable layer, and may also comprise an absorbent core, in which case the top layer and bottom layer are folded with respect to the edges of the absorbent core which has an ovoid, oval, rounded triangle, or other shapes. The bottom substrate contains attachment media located on the bottom layer, whilst the top substrate has support media located towards its top end and bottom end. The bottom and top substrates are held together throughout the periphery. The substrates comprising the absorbent article may or may not have wings. The invention may comprise substrates having a distributing layer located between the top layer and the absorbent core. The bottom layer of the top substrates may be liquid permeable.

DETAILED DESCRIPTION

The present invention relates to an absorbent article comprised of at least two adjacent substrates, preferably one on top of the other, one of them being the top substrate (4) and the other the bottom substrate (5). If the article is comprised of three or more substrates, the middle substrates are located between the top substrate (4) and bottom substrate (5). Each substrate has several fasteners (9), giving the user flexibility in order to place the absorbent article in two positions. In addition, the absorbent article described herein is adaptable to several types of underwear, thus providing the user more flexibility for use with different types of underwear.

Figure 1:
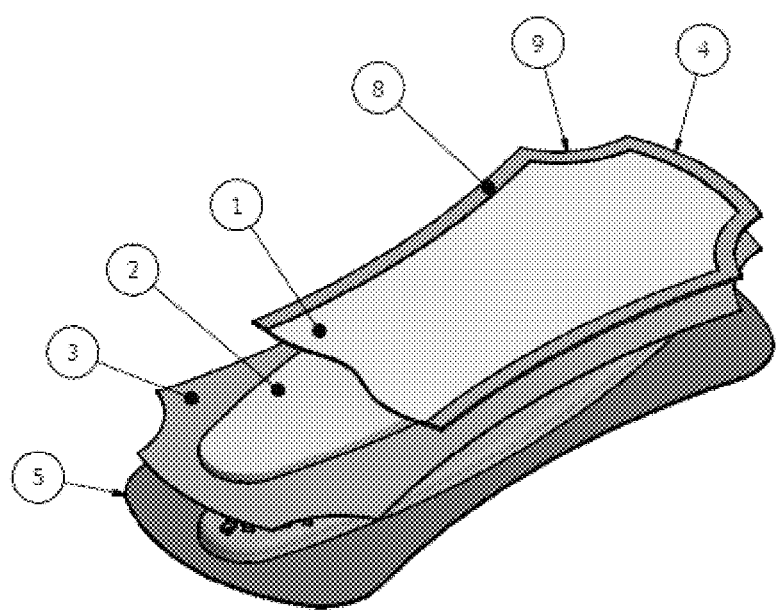
FIG. 1. Illustrates the different substrates which comprise the absorbent article.

According to FIG. 1, in one embodiment of the invention, the substrates of the absorbent article are located one on top of the other in such a manner that the top layer (1) of the top substrate (4) contacts the user. The bottom layer (3) of the top substrate (4) contacts the top layer (1) of the bottom substrate (5). Each substrate is comprised of a liquid permeable top layer (1), an absorbent core (2) and a bottom layer (3).

The bottom layer (3) is liquid-impermeable and contacts the underwear or the top layer (1) of the bottom substrate (5). The bottom layer (3) avoids that fluids absorbed by the top substrate (4) reach the underwear or come into contact with the bottom substrate (5). Absorbent core (2) is found between the top layer (1) and the bottom layer (3) which is comprised of one or more layers, of one or more materials such as pulp, tissue, SAP and blends thereof, in order to absorb and retain captured fluids.

In an embodiment of the invention, the bottom layer (3) present in the top substrates (4) may be liquid permeable in order to provide greater absorption capacity to the absorbent core.

In an embodiment of the invention, the substrate does not have an absorbent core (2) and only comprises a top layer (1) and a bottom layer (3), wherein the top layer (1) absorbs and retains fluids.

In an embodiment of the invention (not illustrated), the top substrates (4) randomly have an absorbent core (2) between the top layer (1) and the bottom layer (3).

In an embodiment of the invention (not illustrated), a distributing layer is located between the top layer (1) and the absorbent core (2) which is in charge of distributing fluids that are absorbed by the absorbent core (2).

According to FIG. 1, top substrate (4) and bottom substrate (5) which comprise the absorbent article are located on the periphery (8) in order to avoid fluids leaks from the top substrate (4) towards the bottom substrate (5). The attachment allows to separate the substrates without compromising their integrity. The attachment is possible by mechanical weaving, adhesives, hotmelts, ultrasound or a combination thereof.

Figure 6:
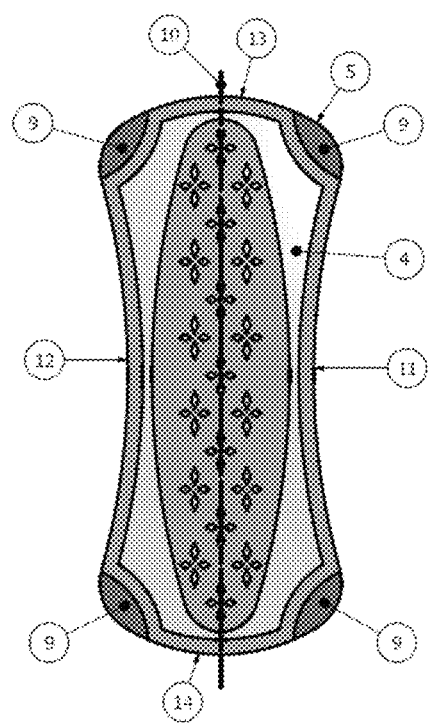

According to FIG. 6, substrates (4) and (5) describe (FIG. 6) an elongated surface having a longitudinal axis (10). On the substrate, four ends are identified, two side ends (11) and (12) located on either side of longitudinal axis (10), and another two ends intersected by the longitudinal axis (10) which correspond to top end (13) and bottom end (14).

According to FIG. 1, substrate (4) comprises fasteners (9). Fasteners (9) can be folds, curled folds, precuts, or strips located on the top layer (1) or bottom layer (3) of the top substrate (4). Through the use of the fasteners (9), the user may easily detach a substrate from the absorbent article by pulling on the substrate intended for detachment. According to FIG. 6, the fasteners (9) are located on the periphery (8) of top end (13) and of bottom end (14) of the top substrate (4).

Figure 2:
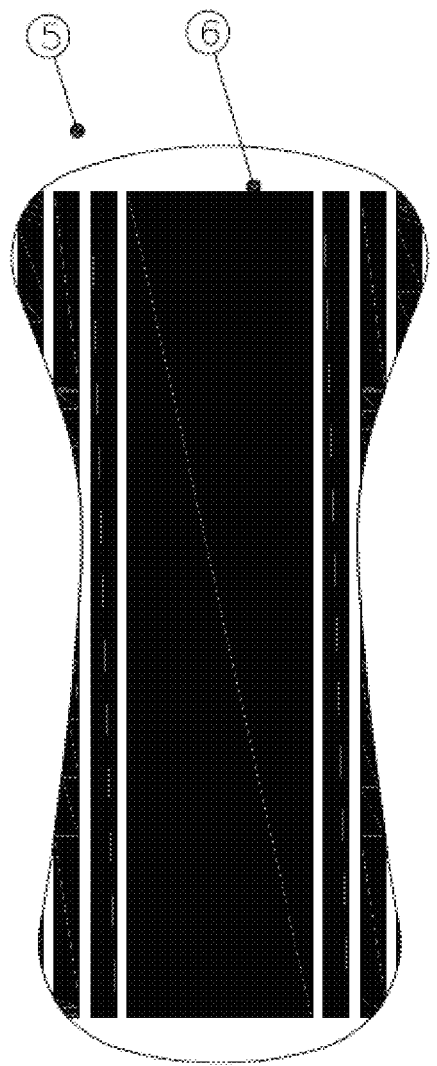
FIG. 2. Illustrates the attachment media of a substrate

In an additional embodiment of the invention, according to FIG. 2, bottom substrate (5) comprises a first adhesive (6) in order to attach the absorbent article to the underwear and thus avoids the absorbent article from moving. The a first adhesive (6) may be adhesives, Velcro, amongst others, and adheres to the bottom layer (3) through the face opposite to the one where the absorbent core (2) is found.

Figure 3:
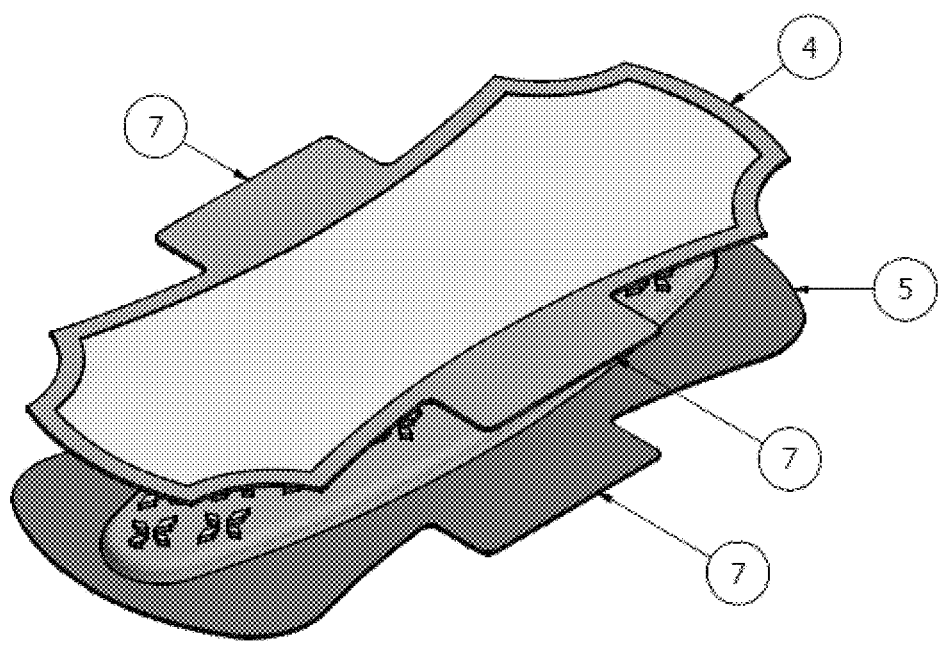
FIG. 3. Embodiment of the invention wherein the absorbent article is comprised of substrates having wings FIG. 4. Embodiment of the invention wherein the absorbent article is comprised of substrates having wings and substrates without wings FIG. 5. Embodiment of the invention wherein the absorbent article is comprised of substrates without wings FIG. 6. Top substrate. Illustrates side borders, bottom end, top end and longitudinal axis of a substrate.

In an embodiment of the invention, according to FIG. 3, substrates (4) and (5) which comprise the absorbent article, have wings (7). The wings (7) of the top substrates (4) may be the same, bigger or smaller in size than the wings (7) of the bottom substrate (5).

Figure 4:
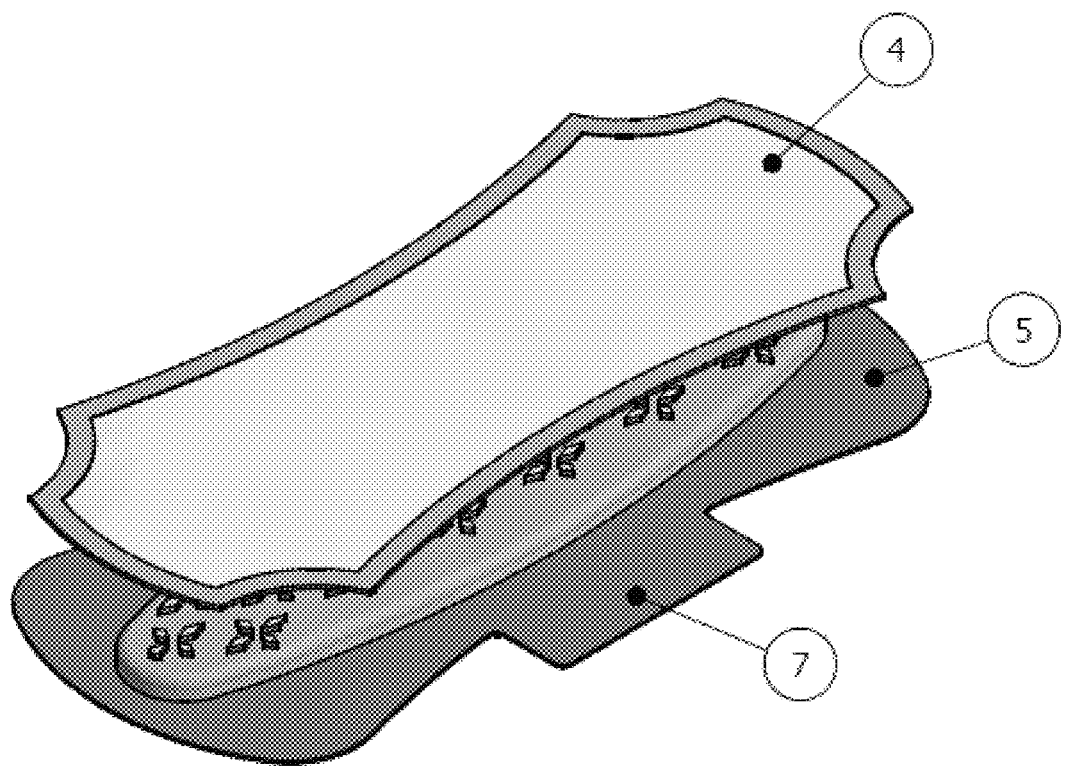

In an embodiment of the invention, according to FIG. 4, the bottom substrate (5) has wings (7) and the top substrates (4) do not have wings (7).

Figure 5:
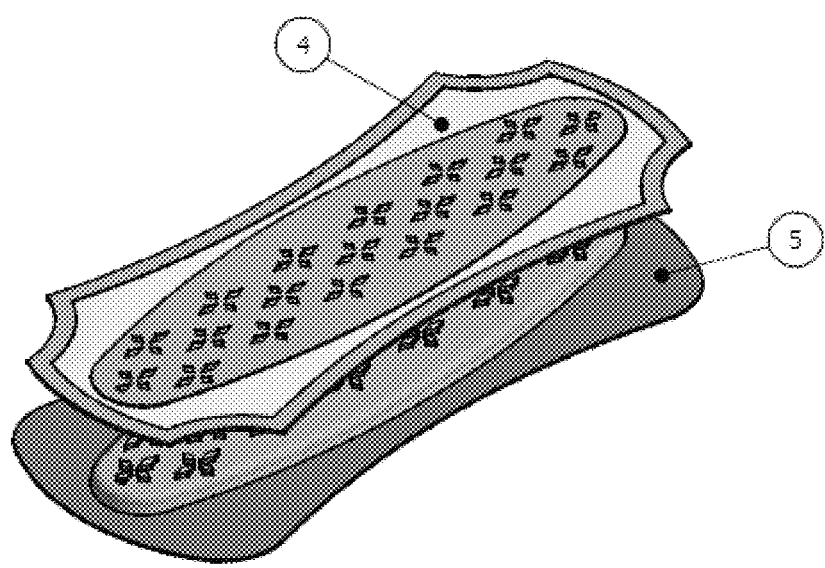

In an embodiment of the invention, according to FIG. 5, the bottom substrate (4) and the top substrate (5) comprising the absorbent article, do not have wings (7).

In an embodiment of the invention (not illustrated), the substrates comprising the absorbent article, alternate in having and not having wings (7).

Figure 7:
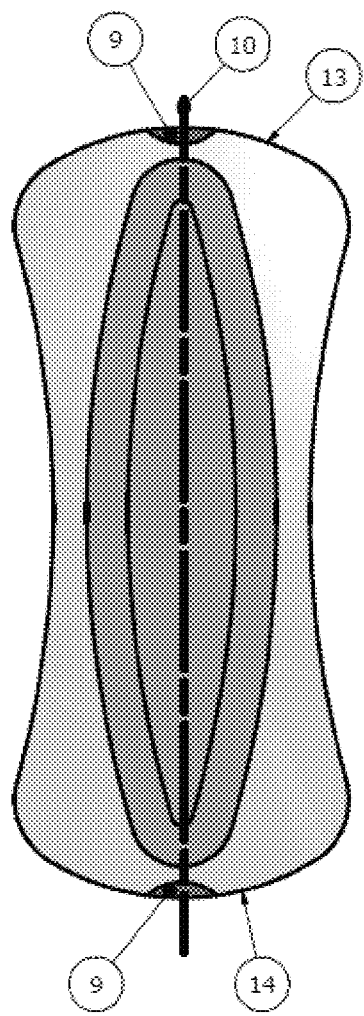
FIG. 7. Embodiment of the invention comprising two support media located over the longitudinal axis, one at the bottom end and the other at the top end of the substrate.

In an embodiment of the invention, according to FIG. 7, each substrate has at least two fasteners (9), one on the top end (13) and another on the bottom end (14) over the longitudinal axis (10). In another embodiment of the invention (not illustrated), the fasteners (9) are located one on the top end (13) and the other on the bottom end (14), not necessarily over the longitudinal axis (10). In an additional embodiment, according to FIG. 6, the substrates have four fasteners (9), two on the top end (13) and two on the bottom end (14).

When fasteners (9) are present on the substrates, both on the top end (13) and bottom end (14), the position for use of the absorbent article is indifferent.

Figure 8:
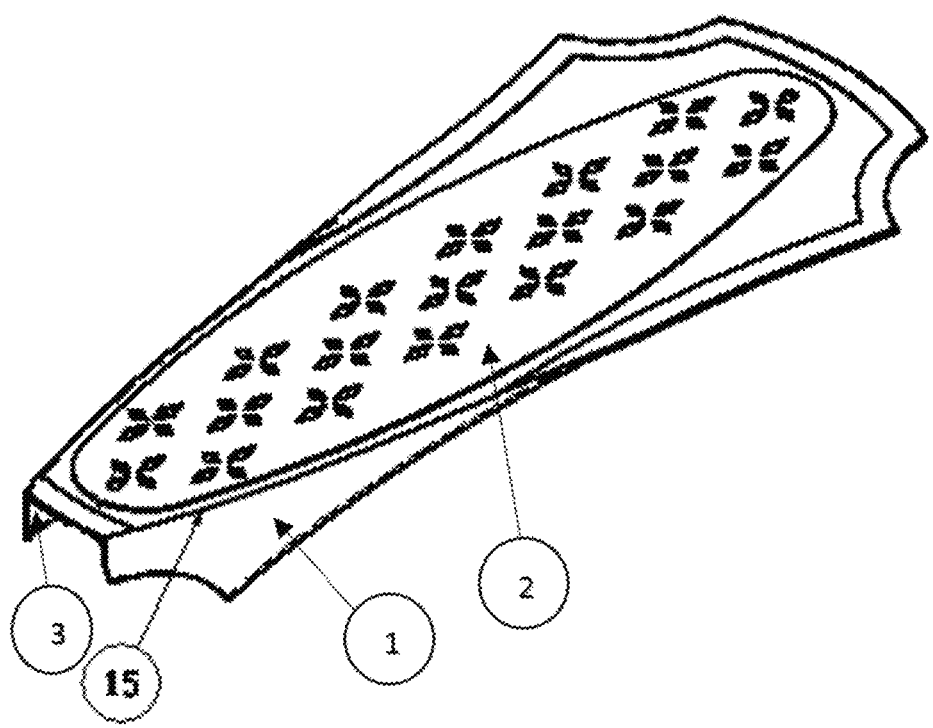
FIG. 8. Illustrates the folding lines with respect to the periphery of the absorbent core which are described when folding the top layer and the bottom layer.

According to FIG. 1, the absorbent core (2) of the top substrate (4) and of the bottom substrate (5) comprising the absorbent article, has an ovoid shape, although it could be oval shaped, rounded triangle shaped, or similarly shaped. In addition, the shape of the absorbent core (2) has a greater thickness than the top layer (1) and bottom layer (3); thus, and according to FIG. 1, the absorbent core (2) describes a volume which can have one of the aforementioned shapes. According to FIG. 8, the shape of the absorbent core (2) allows for the top layer (1) and bottom layer (3) to fold describing the folding lines (15) with respect to the periphery of the absorbent core (2) or underwear; the folding lines (15) are tangential to the periphery of the absorbent core (2).

In an embodiment of the invention (not illustrated), the absorbent core (2) of one or several of the substrates comprising the absorbent article, two portions are observed: a first portion corresponding to a shape located inside the absorbent core (2) and a second portion corresponding to a ring enclosing the first portion. The shape of the first portion of the absorbent core has an ovoid, oval, rounded triangle or similar shape. The shape in the absorbent core allows for the top layer (1), the second portion of the absorbent core (2) and the bottom layer (3) to fold with respect to the periphery of the shape of the first portion of the absorbent core (2), thus describing a folding line (15) with respect to the periphery of the shape of the first portion of the absorbent core (2) or the underwear. Upon projecting said folding lines (15), these do not intersect inside the absorbent article implying that each folding line (15) forms an angle of less than 90° with respect to longitudinal axis (10), and the point where the folding lines (15) intersect will never fall inside the absorbent article.

In an embodiment of the invention (not illustrated), the shape of the absorbent core (2) is asymmetrical with respect to the cross-section axis. Said cross-section axis is perpendicular to the longitudinal axis (10), and therefore, the shape of the absorbent core (2) is an indicator of the position of use.

Figure 9:
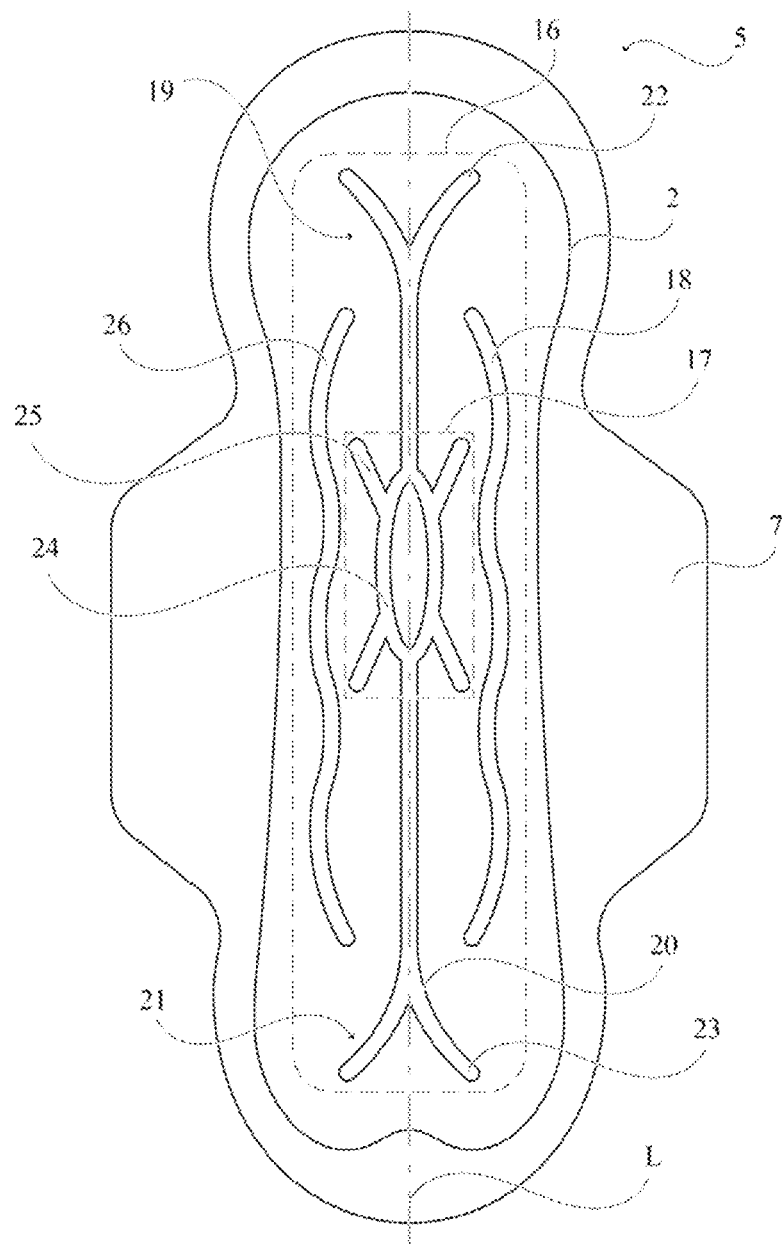
FIG. 9 illustrates an embodiment of a bottom substrate of the disclosed absorbent article. The bottom substrate has wings and an absorbent core, wherein the absorbent core is symmetrical respect to a longitudinal axis and asymmetrical respect to a cross-section axis.
Figure 11:
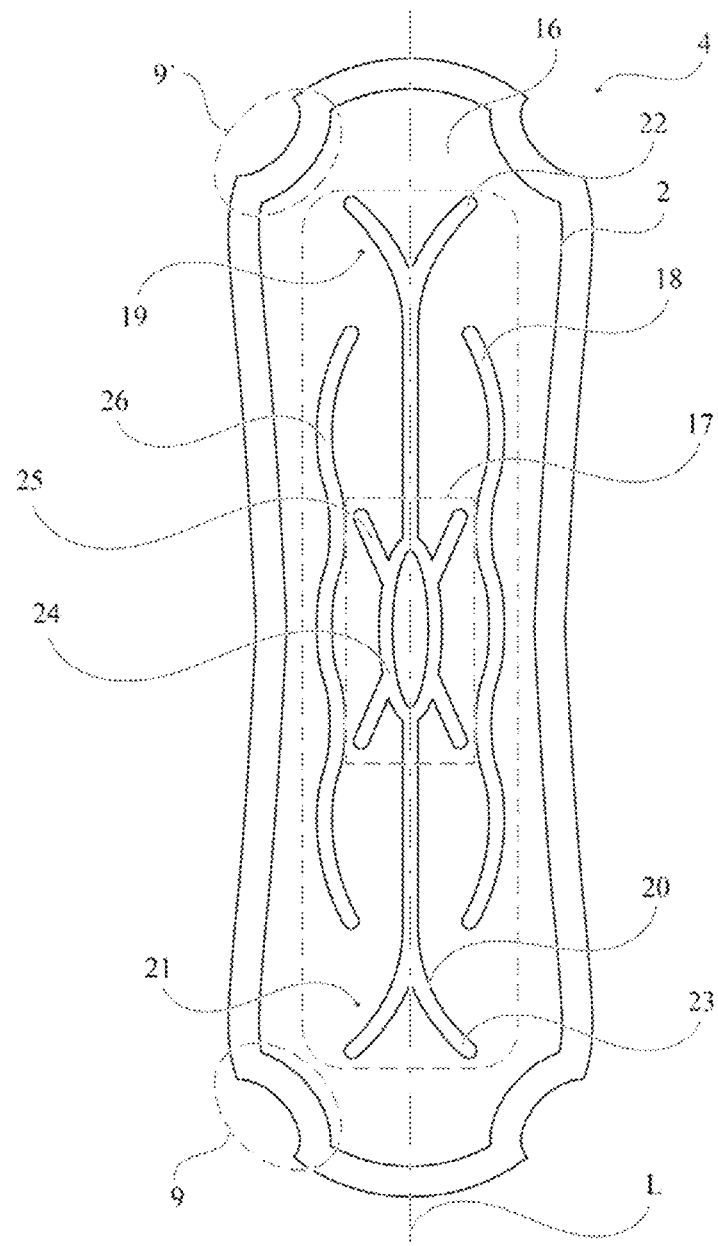
FIG. 11 illustrates an embodiment of a top substrate of the disclosed absorbent article. The top substrate has an absorbent core, wherein the absorbent core is symmetrical respect to a longitudinal axis and also symmetrical respect to a cross-section axis.

Referring to FIGS. 9 and 11, in another embodiment of the absorbent article herein disclosed, any of the top substrate (4) and the bottom substrate (5) may have an absorbent core (2), wherein the absorbent core (2) comprises a channel structure (16) configured to distribute a fluid flux towards a central zone (17) and/or along and across the absorbent core (2).

Accordingly, when a user exudates a fluid flux, for example, of menstrual blood, urine, feces or leukorrheal flux, or other similar flux, the channel structure (16) captures said fluid flux and distribute it along and across the absorbent core (2) of the substrate (4, 5), in order to avoid a wet-like perception of the user in the zone of his/her skin, which be caused beacause of the fluid concentrates in a specific zone of the absorbent core (2).

The channel structure (16) may be formed by a plurality of channels which may or may not be interconnected between them. The channels of the channel structure (16) may extend parallel to the longitudinal axis (L, 10) of the top substrate (4) and bottom substrate (5) or may extend in an angled direction or curved direction respect to the longitudinal axis (L, 10) of the top substrate (4) and bottom substrate (5). The channels may describe a continuous line (curved or straight) or may be formed by discontinuous lines, dots, or patterns having regular or irregular forms.

Some of the channels of the channel structure (16) may extend parallel to the longitudinal axis (L, 10) of the top substrate (4) and bottom substrate (5), and other channels of the channel structure (16) may extend in a different direction. Also, the channels of the channel structure (16) may have similar or different width and depth.

Similarly, the channel structure (16) may have a symmetrical or asymmetrical arrangement of channels, and combinations thereof. For example, FIG. 9 illustrates an embodiment of the bottom substrate (5) having a channel structure (16) with an asymmetrical arrangement of channels, wherein the asymmetry is taken respect to a cross-section axis (no illustrated) which is orthogonal to the longitudinal axis (L, 10).

Figure 10:
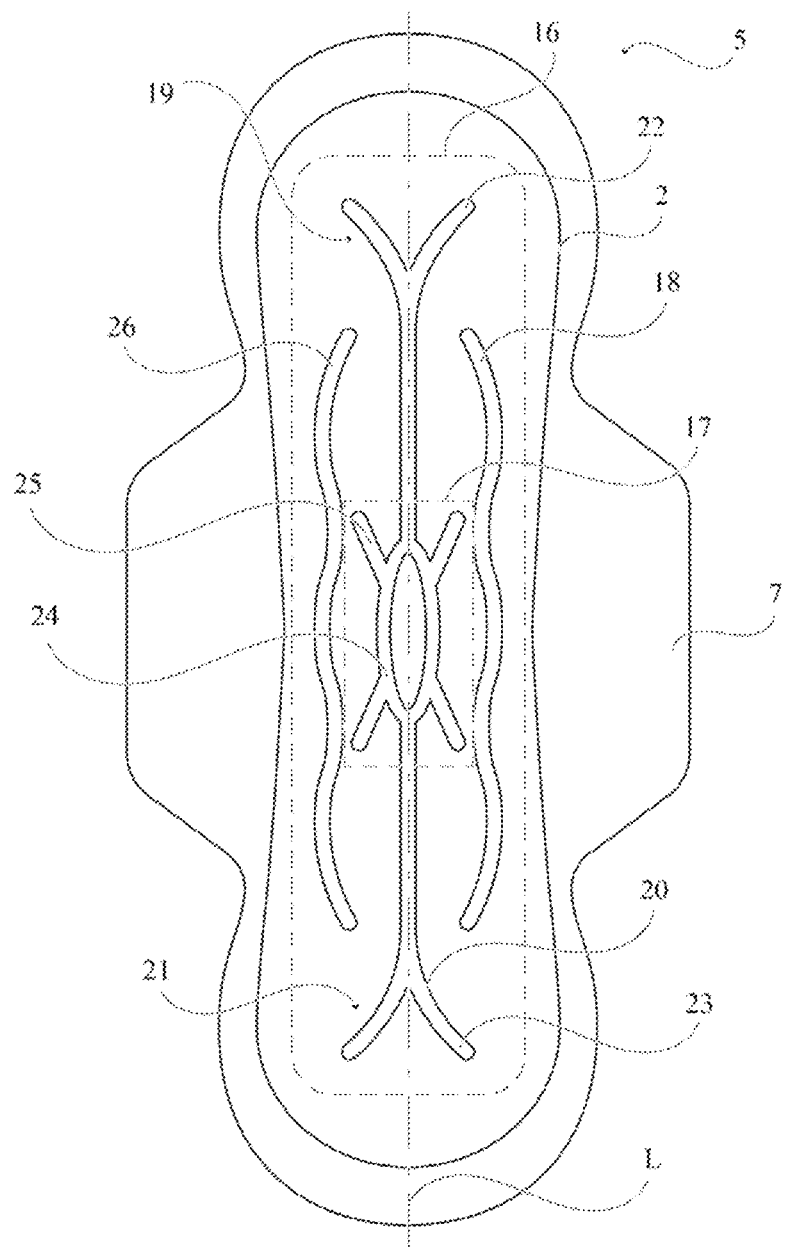
FIG. 10 illustrates an embodiment of a bottom substrate of the disclosed absorbent article. The bottom substrate has wings and an absorbent core, wherein the absorbent core is symmetrical respect to a longitudinal axis and also symmetrical respect to a cross-section axis.

Making reference to FIG. 10, this figure illustrates an embodiment of the bottom substrate (5) having a channel structure (16) with a symmetrical arrangement of channels, wherein the symmetry is taken respect to a cross-section axis (no illustrated) and the longitudinal axis (L, 10).

Similarly, FIG. 11 illustrates an embodiment of the top substrate (4) having a channel structure (16) with a symmetrical arrangement of channels, wherein the symmetry is taken respect to a cross-section axis (no illustrated) and the longitudinal axis (L, 10).

In other non-illustrated embodiments of the top substrate (4), it may have a channel structure (16) with an asymmetrical arrangement of channels.

In various embodiments of the absorbent article may be combined top substrates (4) having a channel structure (16) with symmetrical or asymmetrical arrangements of channels.

The channel structure (16) may be manufactured by embossing processes, where the absorbent core (2) is passed by a nip-roll assembly which forms the channels of the channel structure (16).

Referring to FIG. 9, this figure illustrates an embodiment of the absorbent article (1) where the channel structure (16) may include a central channel (20) having a first channel ramification (17) located in the central zone of the absorbent core (2); a top portion (19) extending from the first channel ramification (17) towards the top end of the top substrate (4) (not illustrated in this figure) and bottom substrate (5) and a bottom portion (21) extending from the first channel ramification (17) towards the bottom end of the top substrate (4) (not illustrated in this figure) and bottom substrate (5).

Referring to FIG. 9-11, the first channel ramification (17) allows distributing a fluid flux which may have been released by a user near the center of the absorbent core (2) Accordingly, the first channel ramification (17) helps to distribute the fluid in the central zone of the absorbent core (2) avoiding fluid leaks caused by excesive fluid concentration near the zone where the user exudates or releases the fluid.

An example of the first channel ramification (17) is shown in FIG. 9. In this figure, the first channel ramification (17) has an ovoid channel (24) having a plurality of ramified channels (25) extending outwardly from the ovoid channel (24). It should be understood that any other shape or number of ramified channels (25) may be used. For example, the ovoid channel (24) may have any other form, for example, circular, rectangular, triangular, octagonal, hexagonal, any other regular or irregular polygon, or any open or closed form comprising curve or straight lines. Similarly, number the ramified channels (25) may be any number, for example, one, two, three, four (as illustrated in FIG. 9), five, or multiples thereof. The ramified channels (25) may describe a continuous line (curved or straight) or may be formed by discontinuous lines, dots, or patterns having regular or irregular forms.

The channel structure (16) may further include a second channel ramification (22) located in the top portion (19). Also, the channel structure (16) may further include a third channel ramification (23) located in the bottom portion (21) of the central channel (20). The second channel ramification (22) and the third channel ramification (23) are configured to distribute fluid in along and across the zones of the absorbent core (2) where are located the top portion (19) and the bottom portion (21).

In a non-illustrated realization of the absorbent article, the channel structure (16) may include the second channel ramification (22) but not the third channel ramification (23). In a non-illustrated realization of the absorbent article, the channel structure (16) may include the third channel ramification (23) but not the second channel ramification (22).

In a realization of the absorbent article, as illustrated in FIG. 9 the channel structure (16) may include the second channel ramification (22) and the third channel ramification (23).

A technical effect of having the second channel ramification (22) and the third channel ramification (23) is that the absorbent article may be placed in underwear of a user in two positions, wherein in each position either the second channel ramification (22) or the third channel ramification (23) would be placed near a body part of the user through where the fluid is exudated or released.

Also, in any of the embodiments of the absorbent article including an absorbent core (2) with a channel structure (16) in either the top substrate (4) or the bottom substrate (5), the absorbent article may include wings (7) in the bottom substrate (5), in the top substrate (4) or both in the bottom substrate (5) and top substrate. For example, FIGS. 9-10 illustrate embodiments of the absorbent article having wings (7) in the top substrate (5).

Making reference to FIG. 10, in a realization of the absorbent article, the absorbent core (2) is symmetrical respect to a longitudinal axis (L, 10) and a cross-section axis (non-illustrated) of the top substrate (4) and bottom substrate (5) (not illustrated in this figure), and wherein the channel structure (16) is symmetrical respect to the longitudinal axis (L) and the cross-section axis of the top substrate (4) and bottom substrate (5). The cross-section axis is perpendicular to the longitudinal axis (L, 10).

In this exemplary embodiment, the symmetrical shape of the channel structure (16) allows the user to attach the absorbent article in her/his underwear in two different directions and having the same fluid distribution effect in the channel structure (16). Accordingly, in this embodiment a user in a rush would not have any risk of installing the absorbent article in a wrong direction.

It should be understood as wrong direction, a direction when the absorbent article has an asymmetric absorbent core (2) having a channel structure (16) with more channels in either the top portion (19) or the bottom portion (21), and the user places the absorbent article in her/his underwear in such a way that the portion (19, 21) having more channels is put away from the part of the body of the user through which is released or exudated a fluid.

Referring to any of FIG. 9-11, in any of the embodiments of the absorbent article including an absorbent core (2) with a channel structure (16) in either the top substrate (4) or the bottom substrate (5), the channel structure includes a first lateral channel (18) and a second lateral channel (26) placed near a lateral edge of the absorbent core (2).

The first lateral channel (18) and the second lateral channel (26) are configured to distribute fluid along the absorbent core (2) in order to avoid liquid leaks through a lateral edge of the absorbent core (2).

For example, FIG. 9 illustrates a realization of the first lateral channel (18) and the second lateral channel (26), wherein each of the first lateral channel (18) and the second lateral channel (26) is substantially linear and parallel to the longitudinal axis (L). Additionally, the first lateral channel (18) and the second lateral channel (26) may have a wavelike or curvy shape as illustrated in FIG. 9, or another equivalent shape.

EXAMPLE 1

Absorbent Article Having a Substrate Including an Absorbent Core (2) With a Channel Structure (16)

Figure 12:
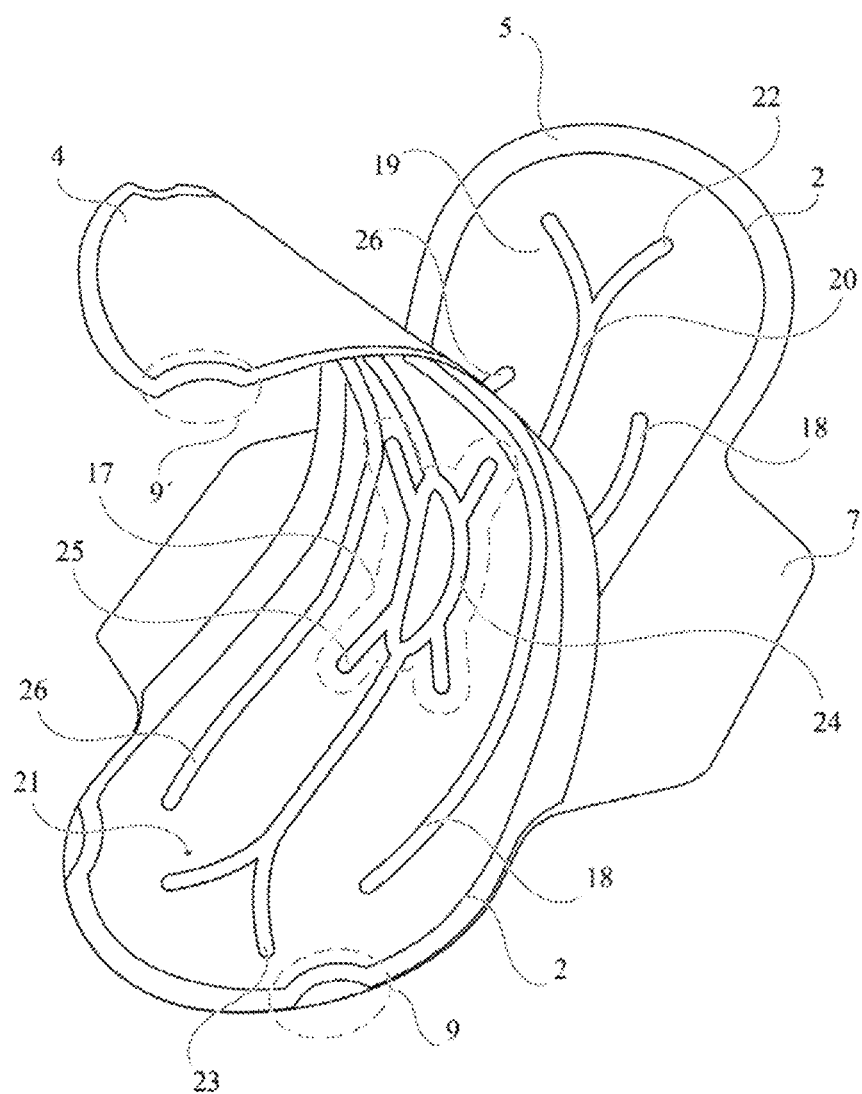
FIG. 12 shows an embodiment of the absorbent article having a bottom substrate and a top substrate being unattached from the bottom substrate. Each of the bottom substrate and the top substrate includes an absorbent core.

Referring to FIG. 12, an embodiment of the absorbent article includes a top substrate (4) located atop a bottom substrate (5). Making reference to FIG. 1, each of the top substrate (4) and the bottom substrate (5) comprises a top layer (1) which is permeable and a bottom layer (3).

Referring to FIG. 2 and FIG. 1, the bottom substrate (5) has a first adhesive (6) located in its bottom layer (3), wherein the bottom layer (3) is impermeable. The first adhesive (6) allows a user to attach the absorbent article to her/his underwear.

The top substrate (4) has a first fastener (9') and a second fastener (9), wherein the first fastener (9') is located in a top end of the top substrate (5) and the second fastener (9) is located in a bottom end of the top substrate (5).

The bottom substrate (4) and the top substrate (5) are held together in their periphery. The attachment between the bottom substrate (4) and the top substrate (5) is possible by mechanical weaving, adhesives, hotmelts, ultrasound or a combination thereof.

Figure 13:
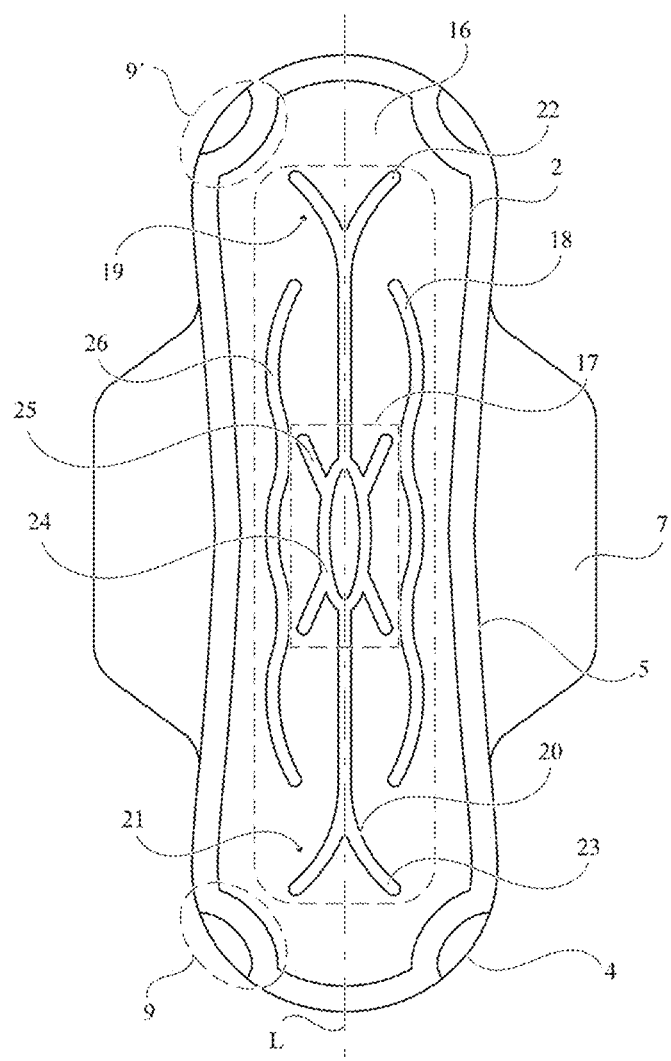
FIG. 13 shows the embodiment of FIG. 12 from a top view, wherein in FIG. 13 the bottom substrate is attached to the top substrate.

Referring to FIG. 13, the first fastener (9') and the second fastener (9) are configured to allow a user placing the absorbent article on her/his underwear in two positions. Making reference to FIG. 12, the first fastener (9') and the second fastener (9) are configured to allow a user and removing the top substrate (4) from the bottom substrate (5) by pulling any of the first fastener (9') or the second fastener (9). For example, in FIG. 12 the top substrate (4) is removed from the bottom substrate (5) by pulling upwardly the first fastener (9').

Referring to FIG. 13, the illustrated example has a channel structure (16) which is symmetrical respect to the longitudinal axis of the top substrate (5) from the bottom substrate (4). Also, the channel structure (16) shown in FIG. 13 is symmetrical respect to a cross-section axis (non-illustrated) which is perpendicular to the longitudinal axis (L, 10).

Accordingly, the symmetrical shape of the channel structure (16) allows the user to attach the absorbent article in her/his underwear in two different directions and having the same fluid distribution effect in the channel structure (16). Accordingly, in this embodiment a user in a rush would not have any risk of installing the absorbent article in a wrong direction.

It must be understood that the present invention is limited to the embodiments described and illustrated herein, and as will be evident to any normally skilled person in the art, possible variations and modifications exist that do not fall outside the scope of the invention, which is solely defined by the following claims.

The invention claimed is:

1. An absorbent article, comprising a top substrate located atop a bottom substrate, each of the top substrate and the bottom substrate including a top permeable layer and a bottom layer, wherein:
   the bottom substrate has a first adhesive located in its bottom layer,
   the top substrate has a first fastener and a second fastener, wherein the first fastener is located in a top end of the top substrate and the second fastener is located in a bottom end of the top substrate;
   wherein the bottom layer of the bottom substrate is impermeable;
   wherein the bottom substrate and the top substrate are held together throughout their periphery;
   wherein the location of the first fastener and the second fastener is configured so a user is able to place the absorbent article on underwear in two positions with either of the first fastener or the second fastener toward the front of the user's underwear, and removing the top substrate from the bottom substrate by grasping and pulling any of the first fastener or the second fastener; and
   wherein the first fastener and the second fastener are selected from the group comprising, folds, curled folds, precuts, strips and combinations thereof.

2. The absorbent article of claim 1, further comprising more than one top substrate.

3. The absorbent article of claim 2, wherein at least one of the top substrates has an absorbent core between its top layer and its bottom layer.

4. The absorbent article of claim 1, wherein any of the top substrate or the bottom substrate further comprises an absorbent core between their top permeable layer and their bottom layer.

5. The absorbent article of claim 1, wherein the top substrate and the bottom substrate have wings, and wherein the wings of the top substrate are of the same size, of smaller size, or bigger size than the wings of the bottom substrate.

6. The absorbent article of claim 1, wherein the top substrate comprises two fasteners on the top end and two fasteners on the bottom end.

7. The absorbent article of claim 1, wherein the fasteners are located on the top permeable layer of the top substrate.

8. The absorbent article of claim 1, wherein the first fastener and the second fastener are located on the bottom layer of the top substrate.

9. The absorbent article of claims 1, wherein any of the top substrate and the bottom substrate has an absorbent core having a shape selected from an ovoid-shape, an oval-shape, a rounded-triangle shape, or a combination thereof.

10. The absorbent article of claim 9, wherein the top layers and the bottom layers of the substrates fold with respect to the periphery of the absorbent core or underwear, describing folding lines which are tangential to the periphery of the absorbent core.

11. The absorbent article of claim 9, wherein the absorbent core contains:
- a first portion of ovoid, oval, rounded-triangle shape or a combination thereof, located inside the absorbent core; and
- a second portion corresponding to a ring enclosing the first portion.

12. The absorbent article of claim 11, wherein the top permeable layers, bottom layers and the second portion of the absorbent core of the substrates fold with respect to the periphery of the shape of the first portion of the absorbent core, describing folding lines at an angle of less than or equal to 90° with respect to the longitudinal axis of the substrates and an intersecting point of the folding lines is located outside the absorbent article.

13. The absorbent article of claim 1, wherein the shape of the top substrate and the bottom substrate is asymmetrical to a cross-section axis.

14. The absorbent article of claim 1, wherein the bottom layer of the top substrate is impermeable.

15. The absorbent article of claim 1, wherein any of the top substrate and the bottom substrate has an absorbent core, wherein the absorbent core comprises a channel structure configured to direct a fluid flux towards a central zone of the substrate.

16. The absorbent article of claim 15, wherein the channel structure includes a central channel having:
- a first channel ramification located in the central zone of the absorbent core;
- a top portion extending from the first channel ramification towards the top end of the top substrate and bottom substrate, and
- a bottom portion extending from the first channel ramification towards the bottom end of the top substrate and bottom substrate.

17. The absorbent article of claim 16, wherein the channel structure further includes:
- a second channel ramification located in the top portion and,
- a third channel ramification located in the bottom portion of the central channel.

18. The absorbent article of claim 15, wherein the channel structure includes a first lateral channel and a second lateral channel placed near a lateral edge of the absorbent core, wherein the first lateral channel and the second lateral channel are configured to avoid liquid leaks through the lateral edge of the absorbent core.

19. The absorbent article of claim 15, wherein the absorbent core is symmetrical respect to a longitudinal axis and is symmetrical respect to a cross-section axis of the top substrate and bottom substrate, and
wherein the channel structure is symmetrical respect to the longitudinal axis and is symmetrical respect to the cross-section axis of the top substrate and bottom substrate.

20. The absorbent article of claim 1, wherein the top substrate or the bottom substrate has wings.

* * * * *